United States Patent [19]

Noack

[11] Patent Number: 4,483,925
[45] Date of Patent: Nov. 20, 1984

[54] LIQUID REMOVAL DEVICE

[75] Inventor: William L. Noack, Camarillo, Calif.

[73] Assignee: Becton, Dickinson and Company, Paramus, N.J.

[21] Appl. No.: 454,760

[22] Filed: Dec. 30, 1982

[51] Int. Cl.$^3$ .................. G01N 33/48; G01N 37/00
[52] U.S. Cl. .................. 435/293; 435/294; 436/809; 422/99; 422/104; 422/101; 141/110
[58] Field of Search .......... 422/99, 101, 102, 104; 436/809; 435/293, 300, 301, 294, 295; 141/110, 111, 112

[56] References Cited

U.S. PATENT DOCUMENTS 4,252,897  2/1981  Axford et al. .................. 435/34
4,351,800  9/1982  Kopp et al. .................. 422/70

FOREIGN PATENT DOCUMENTS 1522128  8/1978  United Kingdom .................. 422/61

Primary Examiner—Barry S. Richman
Assistant Examiner—Joseph P. Carrier
Attorney, Agent, or Firm—Richard J. Rodrick; Richard E. Brown

[57] ABSTRACT

A liquid removal device comprises an absorbent support member and a plurality of tapered liquid absorbent elements. These absorbent elements project from the support member and are adapted to be placed in a liquid-containing vessel for removal of liquid therefrom.

13 Claims, 3 Drawing Figures

LIQUID REMOVAL DEVICE

BACKGROUND OF THE INVENTION

1. Field of the Invention

The present invention relates to a device for removing liquid from a liquid-containing vessel, and more particularly, concerns a device for removing liquids from a plurality of separated liquid-containing wells, such as a standard 96 well tissue culture plate.

2. Description of the Prior Art

In many laboratory procedures, particularly those involving the transfer of liquid media, standard tissue culture plates are employed for holding small quantities of liquids. Standard 96 well tissue culture plates are used for the retention of small quantities of liquid in each of the wells which are separated from each other so that different tests may be carried out using the contents of individual wells. Many procedures require that a certain amount of liquid be removed from all wells of the culture plate, such as the routine feeding of cells cultured in vitro in the 96-well plates, wherein approximately one-half of the culture media is removed from each well and then replaced with fresh media. Present methods of transferring liquid require the pipetting of each well to remove the excess liquid therefrom. It is appreciated that these methods are labor intensive less accurate and present the possibility of cross contamination due to dripping, spillage or the like. Instead of pipetting procedures, attempts have been made recently to utilize fibrous filter material which is dipped into each well for absorbing excess liquids therefrom. However, some type of press device is usually required for inserting the fibrous filter into the plurality of wells; furthermore, these fibrous filter materials are prone to particulate contamination. In addition, this type of filter requires a filter paper on the wicking end of the material to prevent cells from being absorbed into the fibers and further presents a full diameter of surface area at the initial insertion of the material into the wells. This structure has an inclination to cause liquid overflow out of the wells and cross contamination between wells when this occurs. Accordingly, there is a need for a liquid removal device to remove liquid media simultaneously from wells of a liquid-containing vessel, such as a tissue culture plate, without overflow, cross-contamination, or contamination of the wells with material belonging to the device.

SUMMARY OF THE INVENTION

The liquid removal device of the present invention comprises a support member and a plurality of tapered liquid absorbent elements. These elements project from the support member and are adapted to be placed in a liquid-containing vessel for removal of liquid therefrom.

In a preferred embodiment of the present invention, the device for removing liquids is intended for use with a standard 96 well tissue culture plate. The liquid removal device includes a substantially planar support member and 96 wicking elements integrally connected to and distributed in substantially equally spaced, orthogonally arranged columns and rows over one planar surface of the support member. The wicking elements are preferably conically shaped with the narrowest parts thereof projecting away from the planar surface. The support member and wicking elements are preferably formed of a liquid absorbent, nontoxic, contaminant-free material.

In other embodiments of the present invention, the support member further includes means for controlling the depth that the wicking element may be inserted into the liquid-containing wells. For example, at least two depth guides may project from a planar surface in the same direction as the wicking elements. Generally, these guides are shorter than the wicking elements, and contact the top surface of the 96-well plate away from the individual wells.

In accordance with the principles of the present invention, the absorbent nature of the wicking elements provide for the absorption of the desired amount of liquid to be removed from the plurality of wells in the liquid-containing vessel. The tapered or conical shape of the wicking elements, in addition to the support member, are designed to react rapidly enough to prevent spillage of the liquid when the wicking elements are inserted into the individual wells. It can be appreciated that this rapid liquid absorption prevents cross well contamination of tests being conducted within the plurality of wells. When the wicking elements are placed into the liquid inside the wells, only the liquid in contact with the wicking elements will be absorbed into the elements. Additional absorption capacity for liquid removal is provided by the absorptive nature of the support member to which the wicking elements are connected (at least in one embodiment of the present invention). Once the liquid in each well is absorbed into the wicking element, contact with the liquid therein will be broken at a desired point leaving a level of liquid medium in the bottom of each of the plurality of wells. In the embodiment hereof utilizing the depth control means, such control means can be designed so that they engage the sidewalls of the tissue culture plate prior to insertion of the wicking elements thereby maintaining concentricity of the wicking elements to the diameter of the wells. Furthermore, while maintaining concentricity, the wicking elements will not make contact with the inner walls of the wells assuring no cross contamination. It is intended that the liquid removal device of the present invention will be disposable and manufactured of a non-toxic absorbent and contaminant-free material.

DETAILED DESCRIPTION

Figure 1:
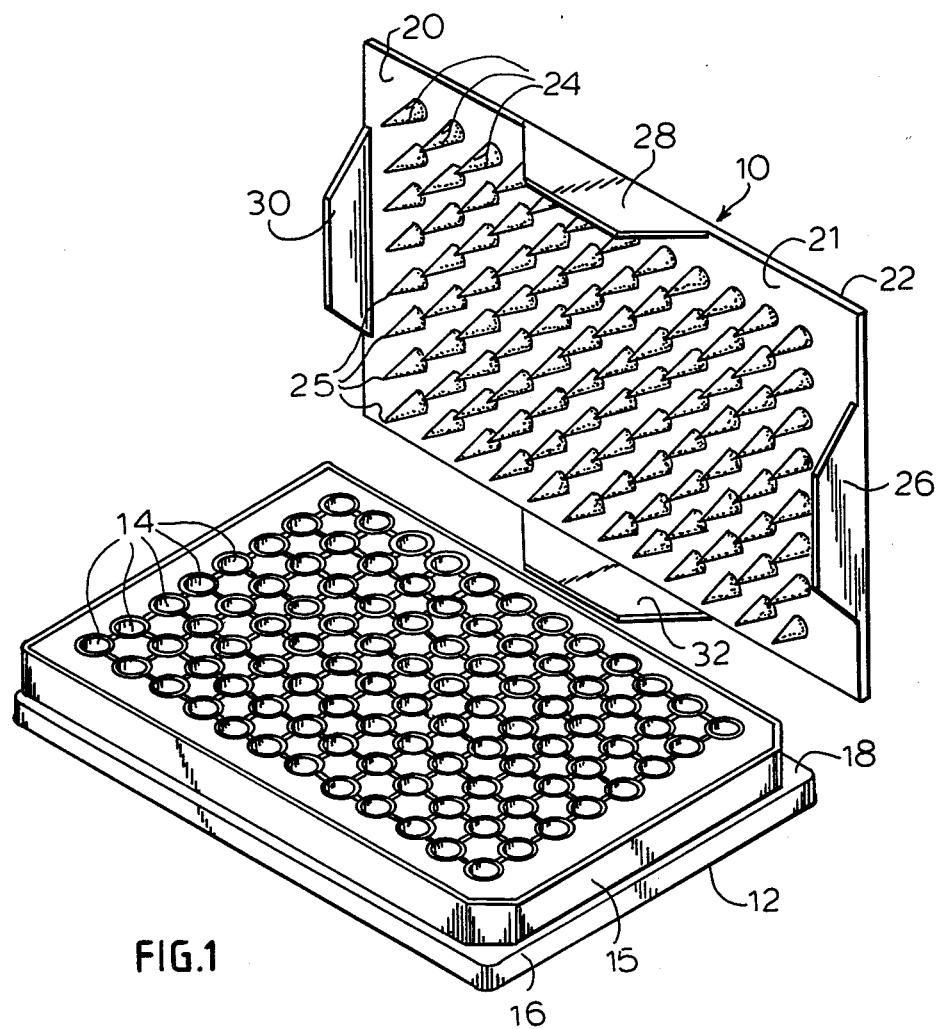
FIG. 1 is a perspective view illustrating the preferred embodiment of the liquid removal device of the present invention in conjunction with and immediately before it is placed in a 96 well tissue culture plate.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Referring now to the drawings, and FIG. 1 in particular, there is illustrated a liquid removal device 10. This device is intended to remove liquids particularly from a vessel containing a plurality of separated liquid-containing wells. Preferably, liquid removal device 10 is used in conjunction with a standard-type 96 well tissue culture plate 12. It can be seen that the tissue culture plate has, in the embodiment being described, 96 wells 14 of substantially equal volume and shape. Wells 14 are arranged in orthogonal columns and rows; in this instance, there are 12 columns each containing 8 rows. An alpha-numeric indicia system is utilized in this embodiment for designating each specific well. It is appreciated that the volume of wells 14 may vary according to the needs of the experiment, and for purposes of the present invention is not a critical parameter. Tissue culture plate 12 also includes an upper sidewall 15 around its entire perimeter. A lower sidewall 16 also surrounds the entire perimeter of the tissue culture plate. A ledge 18 around the entire perimeter of the tissue culture plate lies intermediate the upper and lower sidewalls. It is preferred that the tissue culture plate be made of clear, rigid plastic material, although the choice of materials may vary according to requirements.

Liquid removal device 10 is comprised of substantially planar support member 20. Support member 20 is preferably a thin sheet of material, rectangularly shaped to coincide with the general configuration of the standard 96 well tissue culture plate. In some instances, it is desirable that support member 20 be made of flexible material so that it can be easily fabricated and handled. Of course, in other instances it may be desirable to maintain support member 20 as a rigid structure.

Support member 20 has two flat, planar surfaces, 21 and 22, respectively. Projecting from planar surface 21 is a plurality of wicking elements 24. These wicking elements are specifically intended to absorb and retain liquid which come into contact with same. In the preferred embodiment as being described, wicking elements 24 are conically-shaped projections with the narrowest parts or points 25 projecting away from planar surface 21. Wicking elements 24 are distributed over planar surface 21 in orthogonal columns and rows, and are equally spaced from each other. It is understood that in the embodiment being described, the spacing of the wicking elements on the liquid removal device coincides with the spacing of the wells in the standard 96 well tissue culture plate as previously described. Further, it is preferred that the wicking elements all be substantially the same in size, volume and length, with the points thereof projecting away from planar surface 21.

For the purposes of the present invention, wicking elements 24 may be made of a different material than the support member; the wicking elements may be fabricated together with the support member, or the wicking elements may be subsequently attached to the support member by any suitable, compatible means. However, in the embodiment being described, the wicking elements 24 and support member 20 be fabricated together as a unitary, one-piece, integrally formed structure. As an integral structure, the support member and the wicking elements are fabricated of a liquid absorbent material which readily absorbs liquid first into the conically-shaped wicking elements, and then into the support member for additional absorbent capacity, as will hereinafter be described. Along these lines, it is preferred that the liquid absorbent material out of which the wicking elements are formed, and out of which the entire liquid removal device is formed in the preferred embodiment, be of a non-toxic material, while also being contaminant-free. Materials which satisfy the above criteria are polymeric materials such as polyethylene, polypropylene, PTFE and silicone rubber.

Figure 2:
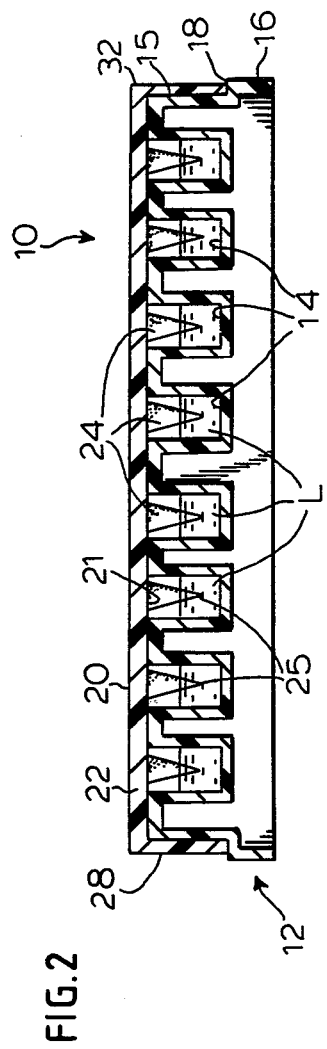
FIG. 2 is a cross-sectional view of the liquid removal device of FIG. 1 positioned on the 96 well tissue culture plate the wells containing excess liquid which is to be removed therefrom.

As seen by referring to FIGS. 1 and 2, the embodiment being described includes four edge surfaces 26, 28, 30 and 32 projecting downwardly from planar surface 21 in the same direction as points 25 of the wicking elements. These surfaces projecting from each edge surface of the support member serve as guides for controlling the depth that the wicking elements are to be inserted into the liquid-containing wells. This feature can be more clearly observed by adverting to FIG. 2.

As seen in FIG. 2, the liquid L has been placed in each of the wells in the tissue culture plate. Each well may have a different liquid medium, or certain constituents of the liquid medium may differ, so that cross contamination of liquid in the separated wells is undesirable. In many instances, tests are to be conducted simultaneously on the liquids in all of the wells. Under these kinds of tests, one control factor is that the amount of liquid in all of the wells be substantially equivalent. Thus, and for example, if each well were preliminary filled with different liquid media, the amounts of liquids may vary from well to well. Therefore excess liquids are to be removed from each well so that the volume of liquid remaining in each well will be substantially uniform and equivalent throughout. To accomplish this, liquid removal device is positioned over tissue culture plate 12 so that wicking elements 24 are inserted into wells 14 in coincidental alignment therewith. Guides 26, 28, 30 and 32 fit around upper sidewall 15 of the tissue culture plate. These guide surfaces rest on ledge 18 of the tissue culture plate which serves as a controlling, abutment stop. This arrangement of the guide surfaces around the wall of the tissue culture plate contributes to maintaining the concentricity of the wicking elements within each of the wells. Furthermore, once guide surfaces 26, 28, 30 and 32 about ledge 18, the penetration of points 25 of the wicking elements in the wells is controlled. As seen in FIG. 2, points 25 have been inserted into liquid L in each of the wells.

Figure 3:
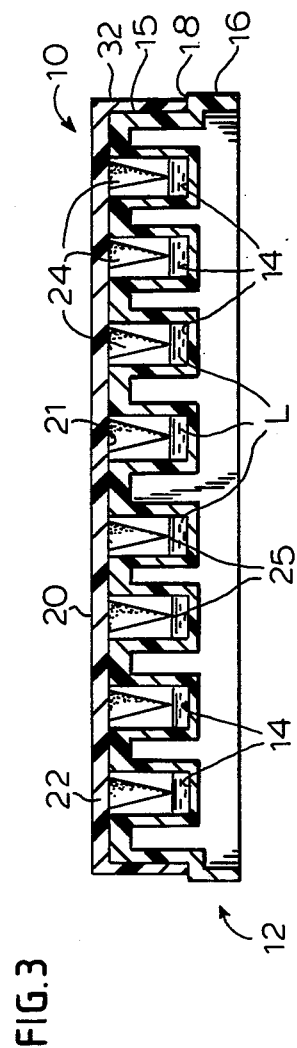
FIG. 3 is a cross-sectional view of the liquid removal device and tissue culture plate illustrating the liquid from the wells absorbed into the liquid removal device.

Turning now to FIG. 3, it can be observed that liquid L has been rapidly absorbed first into wicking elements 24 which project into the wells. In the event that there is more liquid in any particular well than can be absorbed into one wicking element, the absorbent nature of the preferred support member provides reserve absorbent capacity. Thus, in FIG. 3 it can be seen that liquid is absorbed into the wicking elements and also into the support member. By use of the liquid removal device of the present invention, all 96 wells containing excess liquid can have such excess removed simultaneously. Further, once the liquid in contact with the point of each wicking element has been absorbed, liquid will remain in each well determined by the distance from point 25 of the wicking element to the bottom surface of the well. The liquid remaining in this space should therefore be substantially equal in each well. After the liquid removal device of the present invention is removed from the tissue culture plate, tests can be conducted on the liquid in each of the wells.

Thus, the present invention provides a unique liquid removal device for simultaneously removing excess liquids in a plurality of separated liquid-containing wells. Upon removal of this excess liquid from each well, the present invention provides that the liquid remaining in all of the wells should be substantially equal in volume.

What is claimed is:

1. A device for removing liquids from a plurality of separated liquid-containing wells comprising:

a substantially planar support member; and a plurality of wicking elements connected to and distributed over one planar surface of said support member, said wicking elements being conically shaped with the narrowest parts thereof projecting away from said planar surface, and said wicking elements and said support member being formed of a liquid absorbent material, to absorb liquids which come into contact with same.

2. The device of claim 1 wherein said support member and said wicking elements are integrally formed.

3. The device of claim 1 wherein said support member is flexible.

4. The device of claim 1 wherein said wicking elements are all substantially the same in size and volume.

5. The device of claim 1 wherein said wicking elements are substantially equally spaced from each other and are arranged in orthogonal columns and rows.

6. The device of claim 5 wherein there are 96 wicking elements arranged in 12 columns each containing 8 rows.

7. The device of claim 1 wherein said wicking elements are made of a non-toxic and contaminant-free material.

8. The device of claim 7 wherein said material is a polymeric material having an open cellular foam construction 9. A device for removing liquids from a standard 96 well tissue culture plate comprising:

a substantially planar support member and 96 wicking elements integrally connected to and distributed in substantially equally spaced orthogonally arranged columns and rows over one planar surface of said support member, said wicking elements being conically shaped with the narrowest parts thereof projecting away from said planar surface, said support member and wicking elements being formed of a liquid absorbent non-toxic material.

10. The device of claim 9 wherein said support member further includes means for controlling the depth that said wicking elements may be inserted into liquid-containing wells.

11. The device of claim 10 wherein said controlling means includes at least two depth guides projecting from said planar surface in the same direction as said wicking elements.

12. The device of claim 11 wherein there are guides projecting from each edge surface of said support member, said guides being downwardly projecting extensions of said support member.

13. A device for removing liquids from a standard 96 well tissue culture plate comprising:

a substantially planar support member and 96 wicking elements integrally connected to and distributed in substantially equally spaced orthogonally arranged columns and rows over one planar surface of said support member, said wicking elements being conically shaped with the narrowest parts thereof projecting away from said planar surface, said support member and wicking elements being formed of a liquid absorbent, nontoxic material selected from the group consisting of polyethylene, polypropylene, PTFE or silicone rubber, said support member and wicking elements having an open cellular foam construction to absorb an aqueous medium from the 96 wells of a tissue culture plate, and said support member including at least two depth guides projecting downwardly from said planar support member in the same direction as said wicking elements.

* * * * *